(12) United States Patent
Duval et al.

(10) Patent No.: US 11,679,014 B2
(45) Date of Patent: Jun. 20, 2023

(54) DEVICES AND METHODS FOR TREATMENT OF BODY LUMENS

(71) Applicant: Boston Scientific Scimed, Inc., Maple Grove, MN (US)

(72) Inventors: George Wilfred Duval, Sudbury, MA (US); Peter L. Dayton, Brookline, MA (US); Evan Wilder, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 776 days.

(21) Appl. No.: 16/666,624

(22) Filed: Oct. 29, 2019

(65) Prior Publication Data

US 2020/0129318 A1   Apr. 30, 2020

Related U.S. Application Data

(60) Provisional application No. 62/752,574, filed on Oct. 30, 2018.

(51) Int. Cl.
*A61F 5/00* (2006.01)
*A61B 5/06* (2006.01)

(52) U.S. Cl.
CPC ............ *A61F 5/0036* (2013.01); *A61B 5/062* (2013.01)

(58) Field of Classification Search
CPC ....... A61F 5/0036; A61B 5/062; A61B 34/20; A61B 2034/2051; A61B 90/39; A61B 2017/1139; A61B 2090/3945; A61B 2090/3954; A61B 2505/05; A61B 5/6852; A61B 17/1114

USPC .............................. 324/649, 630, 600; 604/8
See application file for complete search history.

(56) References Cited

U.S. PATENT DOCUMENTS

| | | | |
|---|---|---|---|
| 3,051,166 A | 12/1959 | Hovnanian | |
| 6,484,595 B1 * | 11/2002 | Kramer | G01N 13/00 73/866 |
| 8,131,349 B2 | 3/2012 | Okawa et al. | |
| 2008/0058594 A1 | 3/2008 | Xie et al. | |
| 2010/0053312 A1 | 3/2010 | Watanabe et al. | |
| 2010/0105984 A1 * | 4/2010 | Brewer | A61M 25/0127 600/118 |
| 2013/0253550 A1 | 9/2013 | Beisel et al. | |
| 2016/0044873 A1 * | 2/2016 | Jin | A01G 7/04 47/1.3 |
| 2016/0232601 A1 | 9/2016 | Kono et al. | |
| 2017/0296056 A1 * | 10/2017 | Hresko | A61B 5/0015 |
| 2019/0289412 A1 * | 9/2019 | Bervoets | H04R 25/606 |
| 2020/0001048 A1 * | 1/2020 | Oren | A61B 17/00 |
| 2020/0338351 A1 * | 10/2020 | Panken | A61B 5/7221 |
| 2022/0386871 A1 * | 12/2022 | Wu | G01R 33/34092 |

* cited by examiner

*Primary Examiner* — Giovanni Astacio-Oquendo
(74) *Attorney, Agent, or Firm* — Bookoff McAndrews, PLLC

(57) ABSTRACT

A method for performing a medical procedure may comprise advancing a first device through a first body lumen. A distal portion of the first device may include a magnet. The method may further comprise advancing a second device through a second body lumen. The second device may include a magnetic field sensor. The method may further comprise receiving a signal from the magnetic field sensor. The signal may be indicative of a magnetic field measured by the magnetic field sensor. The method may further comprise, if the received signal matches a magnetic field of the magnet, identifying a position of the magnet.

20 Claims, 7 Drawing Sheets

DEVICES AND METHODS FOR TREATMENT OF BODY LUMENS

CROSS-REFERENCE TO RELATED APPLICATIONS

This application claims the benefit of priority from U.S. Provisional Application No. 62/752,574, filed on Oct. 30, 2018, which is incorporated by reference herein in its entirety.

TECHNICAL FIELD

The present disclosure relates generally to devices and methods for diagnosing and/or treating tissue using, for example, endoscopes, bronchoscopes, and ureteroscopes. More specifically, aspects of the present disclosure pertain to devices and methods for positioning medical devices within body lumens of a subject.

BACKGROUND

Endoscopic, bronchoscopic, or ureteroscopic techniques may be used for diagnosing, treating, and/or monitoring conditions by advancing tools and other devices through body lumens. Such techniques may provide treatment options without a need for making incisions in a patient's skin. However, endoscopic devices may be limited in their ability to perform certain procedures due to, for example, difficulties in visualizing areas of interests.

Difficulties may arise, for example, in procedures that involve multiple body lumens or that involve portions of a single lumen separated by tissue walls. For example, in gastric bypass procedures, a portion of a stomach lumen may be connected to a portion of an intestinal lumen such as the jejunum. It may be desirable to create an anastomosis between a particular portion of the jejunum and the stomach. Typical therapeutic and diagnostic endoscopes may be limited in their ability to identify an appropriate portion of the intestine which should be connected to the pouch or other portion of the stomach. For example, an ultrasonic endoscope may have a range that is too small in order to effectively identify the relevant portion of the intestine. For example, an endoscope may be unable to reach the target location and/or the ultrasound may have a range that is unable to visualize (e.g., through a wall of a body lumen) a target location because it is too far away from the ultrasound.

SUMMARY

Examples of the present disclosure relate to, among other things, devices and methods for identifying and/or detecting portions of a body lumen of a subject. Each of the examples disclosed herein may include one or more of the features described in connection with any of the other disclosed examples.

In one example, a method for performing a medical procedure may comprise advancing a first device through a first body lumen. A distal portion of the first device may include a magnet. The method may further comprise advancing a second device through a second body lumen. The second device may include a magnetic field sensor. The method may further comprise_receiving a signal from the magnetic field sensor. The signal may be indicative of a magnetic field measured by the magnetic field sensor. The method may further comprise, if the received signal matches a magnetic field of the magnet, identifying a position of the magnet.

Any method described herein may include one or more of the features or steps described below. The method may further comprise identifying a location of a tissue wall surrounding the first body lumen. The location may be proximate to the magnet. The first body lumen may be a small bowel lumen. The second body lumen may be a stomach lumen. The method may further comprise joining the first lumen to the second lumen. The signal may include information regarding at least one of a direction or a magnitude of the magnetic field. The magnet may be a diametrical magnet. The first device may include at least one magnetically shielded portion. The second device may further include an atraumatic grasper. The distal portion of the first device may further include a light emitting source. The method may further comprise detecting a light emitted by the light emitting source. The method may further comprise forming a first hole in a first tissue wall defining the first body lumen. The method may further comprise forming a second hole in a second tissue wall defining the second body lumen. The method may further comprise joining the first tissue wall to the second tissue wall. After the first tissue wall and the second tissue wall are joined, the first hole may be in communication with the second hole. The magnetic field may have a direction perpendicular to a tissue wall defining the first body lumen.

In another example, a method for performing a medical procedure may comprise: advancing a first device through a first body lumen to a portion of the first body lumen. A distal portion of the first device may include a magnet. The method may further comprise advancing a second device through a second body lumen. The second device may include a magnetic field sensor. The method may further include receiving a signal from the magnetic field sensor. The signal may be indicative of a magnetic field measured by the magnetic field sensor. Based on the received signal, the portion of the first body lumen may be joined to the second body lumen.

Any method described herein may include one or more of the features or steps described below. The method may further comprise identifying a location of a tissue wall surrounding the first body lumen. The location may be proximate to the magnet. The first body lumen may be a small bowel lumen. The second body lumen may be a stomach lumen. The method may further comprise grasping a wall surrounding the first body lumen proximate to the portion of the first body lumen. The magnetic field may have a direction perpendicular to a tissue wall defining the first body lumen.

In a still further example, a method for performing a medical procedure may comprise: advancing a first device through a first body lumen. A distal portion of the first device may include a magnet. The method may further comprise advancing a second device through a second body lumen. The second device may include a magnetic field sensor. The method may further comprise receiving a signal from the magnetic field sensor. The signal may be indicative of a magnetic field measured by the magnetic field sensor. Based on the received signal, a medical tool may be advanced from the second body lumen into the first body lumen.

Any method described herein may include one or more of the features or steps described below. The method may further comprise identifying a location of a tissue wall surrounding the first body lumen. The location may be proximate to the magnet. The first body lumen may be a small bowel lumen. The second body lumen may be a stomach lumen. The magnetic field may have a direction perpendicular to a tissue wall defining the first body lumen.

In another example, a system for performing a medical procedure may comprise a first device. A distal portion of the first device may include a magnet having a magnetic field. The first device may be configured to be advanced into a first body lumen. The system may also comprise a second device. The second device may include a magnetic field sensor. The magnetic field sensor may be configured to transmit a signal indicative of a magnetic field measured by the magnetic field sensor. The signal may be compared to one or more parameters relating to the magnetic field of the magnet, for identifying a position of the magnet.

Any system described herein may include one or more of the features described below. The signal may include information regarding at least one of a direction or a magnitude of the magnetic field. The magnet may be a diametrical magnet. The first device may include at least one magnetically shielded portion. The first device may include at least one magnetically shielded portion proximal of the magnet and at least one magnetically shielded portion distal of the magnet. The second device may further include an atraumatic grasper. The distal portion of the first device may further include a light emitting source. The second device may include an optical device for detecting the light emitting source. The magnetic field may have a direction perpendicular to a tissue wall defining the first body lumen. The second device may be configured for insertion within a working channel of a sheath. The first body lumen may be a small bowel lumen, and the second body lumen may be a stomach lumen. The first device may include an articulation joint and hand-held controls. The identified position may be indicative of a location of a tissue wall in which a hole is to be formed. The first device may be configured to be positioned so that the magnet is approximately 150 cm distal to a pylorus. The first device may be configured to be inserted into the first lumen at the same time the second device is inserted into the second lumen. The magnetic field sensor may be at least one of a Hall effect sensor, a magnetoresistive sensor, a flux gate, a flux coil, or a magnetoinductive sensor.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "endoscope" may be used herein but is not limiting. References to endoscopes may also include other medical devices, including, but not limited to, bronchoscopes, ureteroscopes, colonoscopes, catheters, sheaths, and the like.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The present disclosure is drawn to devices, systems, and methods for diagnosing and/or treating tissue using, for example, endoscopes, bronchoscopes, ureteroscopes, and other medical devices. More specifically, aspects of the present disclosure pertain to devices and methods for positioning medical devices within body lumens of a subject. In particular, at least in some aspects, the devices, systems, and methods disclosed herein may facilitate identifying and/or detecting portions of a body lumen of a subject. Although gastrointestinal anatomy may be referenced herein, reference to gastrointestinal anatomy should not be construed as limiting possible applications of the disclosed devices and methods. The disclosed devices and methods may be suitable for use in a variety of portions of a subject's body, including, for example, urological organs, the respiratory system, or other portions of the digestive system. And although a gastric bypass procedure may be referenced herein, the disclosed devices and methods may be used for a variety of medical procedures, including any procedure requiring precise location of a position within a body lumen.

Figure 1:
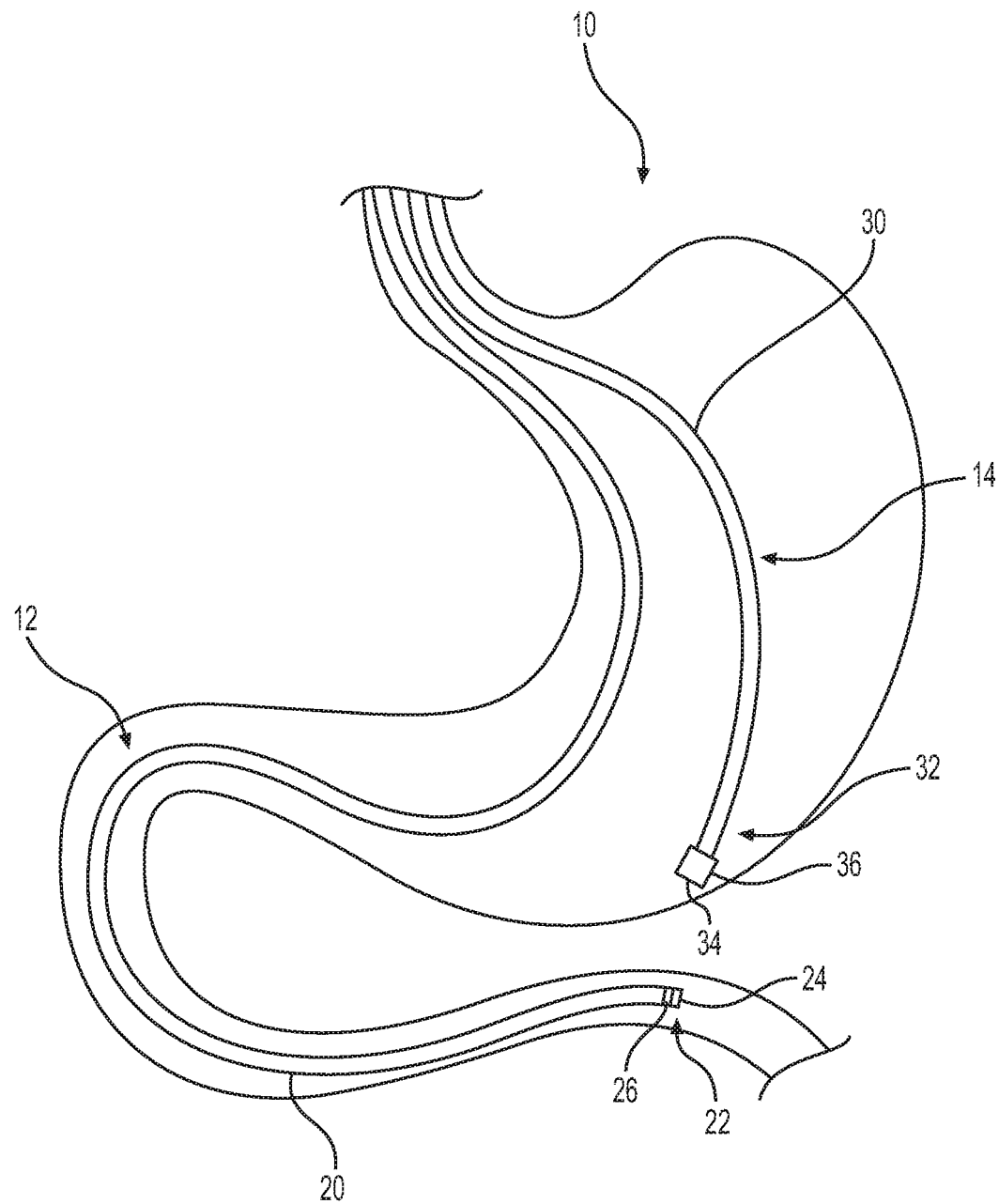
FIG. 1 shows an exemplary system for performing a medical procedure such as a gastroenteral anastomosis procedure.

FIG. 1 depicts an exemplary system 10 for performing a gastric bypass procedure. System 10 may include a first device 12 and a second device 14. Devices 12 and/or 14 may be, for example, endoscopic devices suitable for insertion into a body lumen of a subject. While first device 12 and second device 14 are shown in FIG. 1 as stand-alone devices (e.g., an endoscopic device) inserted directly into a body lumen of a patient, it will be understood that first device 12 and second device 14 may be used in conjunction with other devices. For example, first device 12 and/or second device 14 may be inserted into a body lumen of a patient via a sheath such as an endoscopic sheath. For example, a sheath could be inserted into a body lumen of a patient, and then first device 12 and/or second device 14 could be inserted into a working channel of the sheath.

First device 12 may be insertable into a subject and may include an elongate member or shaft 20. Member 20 may be made of a flexible material that is suitable for use inside a body lumen of a subject. Member 20 may be steerable via, for example, hand-held controls external to the body and an articulation joint at a distal end of member 20. Alternatively, member 20 may be passively bendable in a body lumen of a subject. Member 20 may have a distal portion 22. Distal portion 22 may include any suitable mechanisms for visualizing and/or navigating a body lumen of a subject. For example, distal portion 22 may include a lighted portion, a camera, or any other suitable device. Alternatively, first device 12 may be configured to be inserted along with another device that includes mechanisms for steering and/or navigating. For example, first device 12 may be inserted in a working channel of a sheath such as a sheath of an endoscope. First device 12 may remain in a body lumen of a subject after such an insertion device is removed from the body lumen. Alternatively, both first device 12 and an insertion device or mechanism for navigating first device 12 may remain in a body lumen of a patient. A distal portion 22 of first device 12 may include a distal tip 24. Distal tip 24 may have atraumatic features, such as a rounded tip, in order to avoid damage to tissues of a body lumen of a subject. Distal tip 24 may additionally or alternatively have openings for lighting and/or video mechanisms and/or openings for irrigation, suction, insufflation, or other functionality. For example, distal tip 24 may include openings for one or more LEDs, cameras, lenses, optical fibers, etc.

Distal portion 22 (or another portion of first device 12) may also include a magnetic device 26. Magnetic device 26 may be a permanent magnet or may be activated by a current running through wires of shaft 20 and magnetic device 26. Magnetic device 26 may have a known magnetic field such as, for example, the magnetic field discussed below with regard to FIGS. 3A-3C. In particular, a field of magnetic device 26 may be known in a region between magnetic device 26 and a stomach lumen of a subject, when first device 12 is inserted into a portion of a small intestine of the subject, as shown in FIG. 1. For example, a magnetic field in a stomach lumen in a region near a major curvature or a pylorus of a subject's stomach may be known. For example, a general shape of the field, a general strength of the field, etc. may be known. For example, it may be known that the strongest magnetic field corresponds to a particular location of the magnetic device 26. While exemplary magnetic fields are discussed below, a variety of magnetic field configurations may be suitable for the devices, systems, and methods disclosed herein.

Second device 14 may be insertable into a subject and may include an elongate member 30. Member 30 may be made of a flexible material that is suitable for use inside a body lumen of a subject. Member 30 may be steerable via, for example, hand-held controls external to the body and an articulation joint at a distal end of member 30. Alternatively, elongate member may be passively bendable in a body lumen of a subject. Member 30 may have a distal portion 32. Distal portion 32 may include any suitable mechanisms for visualizing and/or navigating a body lumen of a subject. For example, distal portion 32 may include a lighted portion, a camera, or any other suitable device. Alternatively, second device 14 may be configured to be inserted along with another device that includes mechanisms for steering and/or navigating. For example, second device 14 may be inserted in a working channel of a sheath such as a sheath of an endoscope. Second device 14 may remain in a body lumen of a subject after such an insertion device is removed from the body lumen. Alternatively, both second device 14 and an insertion device or mechanism for navigating second device 14 may remain in a body lumen of a patient. A distal portion 32 of second device 14 may include a distal tip 34. Distal tip 34 may have atraumatic features, such as a rounded tip, in order to avoid damage to tissues of a body lumen of a subject. Distal tip 34 may additionally or alternatively have openings for lighting and/or video mechanisms and/or openings for irrigation, suction, insufflation, or other functionality. For example, distal tip 34 may include openings for one or more LEDs, cameras, lenses, optical fibers, etc.

Distal portion 32 (or another portion of second device 14) may also include a magnetic field sensor 36. Magnetic field sensor 36 may be any suitable type of magnetic field sensor known in the art, such as, for example, a Hall effect sensor, a magnetoresistive sensor, a flux gate or coil, or a magnetoinductive sensor. Magnetic field sensor 36 may measure one or more of a magnitude or direction of a magnetic field. The above types of magnetic field sensors are merely exemplary and are not limiting. Magnetic field sensor 36 may be any type of sensor configured to measure a magnetic field. Magnetic field sensor 36 may measure a direction and/or magnitude of a magnetic field emitted by magnetic device 26. Magnetic field sensor 36 may be configured to transmit a signal regarding a direction and/or a magnitude of a measured magnetic field. A controller may be configured to compare the signal to one or more parameters relating to known features (e.g., direction or strength) of the magnetic field of the magnet, for identifying a position of the magnet. Alternatively, the signal measured by magnetic field sensor 36 may be compared to one or more parameters related to the magnetic field of magnetic device 26, such as by manual comparison by an operator or by other means. The compared parameters may be used to identify a location or position of magnet 26, as described herein (e.g., by use of a direction of a magnetic field of magnet 26 or a magnitude of a direction of a magnetic field of magnet 26). Magnetic field sensor 36 may additionally or alternatively be configured to identify when a region of the largest measured magnetic field has been identified.

Second device 14 may be advanced into a stomach of a subject so that distal portion 32, including magnetic field sensor 36, is positioned in a known or otherwise predetermined area of the stomach (e.g., near a wall of the stomach proximate to the greater curvature, antrum, and/or the pylorus). For example, distal portion 32 may be advanced to a portion of the stomach where a bypass procedure will be performed in order to connect a pouch of the stomach to the ileum or other portion of the small intestine.

First device 12 may be advanced though a subject's small intestine until a known or otherwise predetermined portion of the small intestine is reached. For example, it may be desirable to perform a gastric bypass between the stomach and a portion of the small intestine approximately 150 cm past the pylorus. First device 12 may include markings or other features which enable a user to advance first device 12 to a known position (e.g., approximately 150 cm past the pylorus). For example, hash markings or ruler-type markings may be used on a portion of first device 12 such as an outer jacket or catheter so that, after the marked portion of device 12 reaches the end of an endoscope used for insertion of device 12, the markings can be used to measure how far device 12 extends into the jejunum. Additionally or alternatively, a shaft of first device 12 may change color at a distance of 150 cm so that the distance of the pylorus is obvious by looking at the color of a shaft of first device 12 at the pylorus.

Second device 14 may then be maneuvered in a stomach lumen until magnetic field sensor 36 obtains a reading indicative that magnetic field sensor 36 is adjacent to magnetic device 26. In this way, it may be determined that magnetic field sensor 36 is adjacent to magnetic device 26, despite the fact that two tissue walls (e.g., a wall of the stomach and a wall of the ileum) may be in between magnetic field sensor 36 and magnetic device 26. Additionally or alternatively, second device 14 may be moved relative to first device 12, and attributes of a magnetic field may be measured by magnetic field sensor 36. A strengthening magnetic field may be indicative that magnetic field sensor 36 is growing nearer to magnetic device 26 along any relevant dimension. For example, if a magnetic field of magnetic device 26 is configured to be detectable in a direction substantially perpendicular to magnetic device 26

(for example, because portions of the field emitting in other directions are shielded, as discussed herein), a measured magnetic field may increase in strength (either gradually or sharply) when magnetic field sensor 36 is proximate to magnetic device 26. For example, an area of the strongest measured magnetic field may be an area that is closest to magnetic device 26. Further details of methods for using first device 12 in conjunction with second device 14 will be discussed below.

Figure 2:
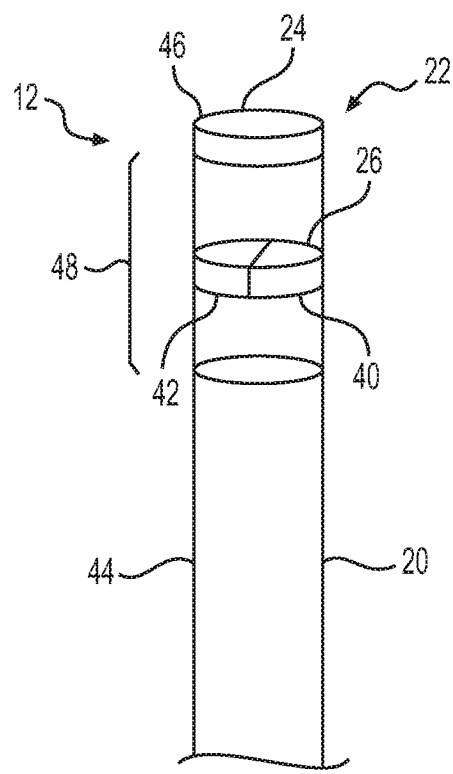
FIG. 2 shows an exemplary distal portion of an endoscope for use with a system for performing medical procedure such as a gastroenteral anastomosis procedure.

FIG. 2 depicts further details of a distal portion 22 of first device 12. As shown in FIG. 2, and discussed above, distal portion 22 may have a distal tip 24 and a magnetic device 26. Magnetic device 26 may be a permanent magnet or an electromagnet. The two poles of magnetic device 26 may be oriented in any suitable manner. For example, magnetic device 26, as shown in FIG. 2, may be a diametric magnet. Magnetic device 26 may have a round perimeter, and the poles, 40 and 42, of magnetic device may be located on opposite sides of a diameter of magnetic device 26. For example, magnetic device 26 may include a first pole 40 that occupies an area of magnetic device 26 on one side of a diameter of magnetic device 20. First pole 40 may be, for example, a north pole of magnetic device 26. Magnetic device 26 may also include a second pole 42 that occupies an area of magnetic device 26 on the other side of a diameter of magnetic device 26 opposite of first pole 40. Second pole 42 may be, for example, a south pole of magnetic device 26. Alternatively, magnetic device 26 may be round but may have poles aligned along a radius of magnetic device 26 (e.g., an inner portion of magnetic device 26 may have one pole, where an outer portion of magnetic device 26 may have another pole) or may have poles divided along a height of magnetic device 26 (e.g., a magnetic device 26 may be split in half along a height of magnetic device 26 so that each pole has a circular, cylindrical, disk-like shape). Alternatively, magnetic device 26 may have other shapes and configurations of poles. For example, magnetic device 26 may be cylindrical, washer-shaped, polygonal, pyramid-shaped, cone-shaped, or prism-shaped.

A portion of shaft 20 of first device 12 that is proximal of magnetic device 26 may include a magnetic shielding. Magnetically shielded portion 44 may extend proximally from a position 0.5 cm-1 cm proximal of magnetic device 26. Magnetically shielded portion 44 may extend proximally to an operation portion (e.g., a handle or actuator) that is proximal to shaft 20. Alternatively, magnetically shielded portion 44 may extend proximally only partially along shaft 20. For example, magnetically shielded portion 44 may extend to a portion of shaft 20 where the effects of magnetic device 26 may no longer be substantially felt. Magnetically shielded portion 44 may include a coating on a surface of shaft 20. Magnetically shielded portion 44 may include, for example, a film coated on shaft 20. Alternatively, magnetically shielded portion 44 may be a portion of shaft 20 that is formed from a different material than other portions of shaft 20. Any suitable material may be used to form magnetically shielded portion 44. For example, magnetically shielded portion 44 may be formed from a metallic thin film including, for example, nickel, aluminum, or other metallic materials that offer magnetic shielding. Additionally or alternatively, a small disk could form a shield and may be made of any of the materials above.

A distalmost portion of shaft 20, proximal to distal tip 24, may also include a magnetically shielded portion 46. Magnetically shielded portion 46 may have any of the properties of magnetically shielded portion 44, as discussed above. Magnetically shielded portion 46 may extend from distal tip 24 to a portion of shaft 20 that is a predetermined distance distal of magnetic device 26 (such as 0.5 cm-1 cm from magnetic device 26). Alternatively, magnetically shielded portion 46 may not extend all the way to a distal tip 24. Magnetically shielded portion 46 may extend far enough distally to where a field of magnetic device 26 does not extend.

An unshielded portion 48 may be proximate to magnetic device 26. Unshielded portion 48 of device 12 may extend approximately one centimeter each of proximally and distally from magnetic device 26 or may extend for approximately one centimeter in total length, straddling magnetic device 26. The shielding may serve to concentrate the magnetic field of magnetic device 26 in the examples herein. Alternatively, unshielded portion 48 may extend any suitable distance proximally and/or distally from magnetic device 26. Unshielded portion 48 may extend an equidistance in a proximal and distal direction relative to magnetic device 26. Alternatively, unshielded portion 48 may be asymmetrical relative to magnetic device 26. For example, unshielded portion 48 may extend further proximally or further distally relative to magnetic device 26.

Magnetically shielded portions 44 and 46 may block or divert passage of a magnetic field emitted by magnetic device 26 so that a magnetic field may not pass through a wall of member 20 where magnetically shielded portions 44 and 46 are present. In contrast, unshielded portion 48 may allow a magnetic field emitted by magnetic device 26 to pass through the walls of member 20 in the location of unshielded portion 48. A presence of magnetically shielded portions 44 and 46 may cause a magnetic field emitted by magnetic device 26 to take on a more focused shape. For example, in the region of unshielded portion 48, a magnetic field emitted by magnetic device 26 may be mostly or substantially perpendicular relative to a longitudinal axis of member 20. Shielded portions 44 and 46 may block passage of a magnetic field from magnetic portion 26 where the magnetic field would be relatively less perpendicular relative to a longitudinal axis of the member 22.

Figure 3A:
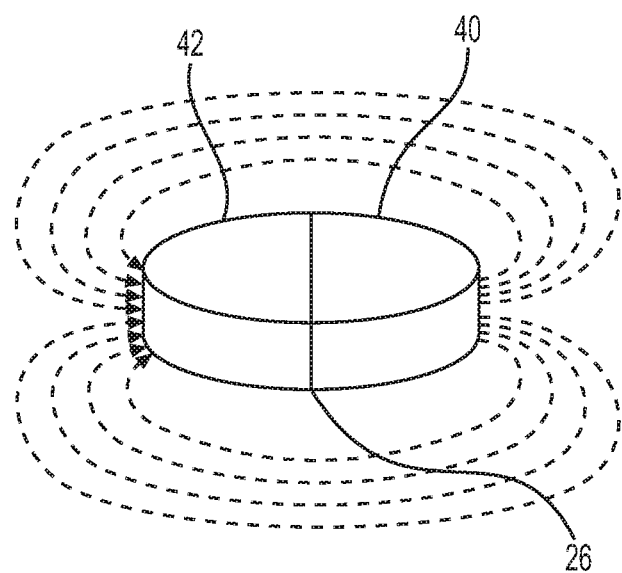
FIGS. 3A-3C show an exemplary magnetic component for use with a system for performing a gastric bypass procedure.
Figure 3B:
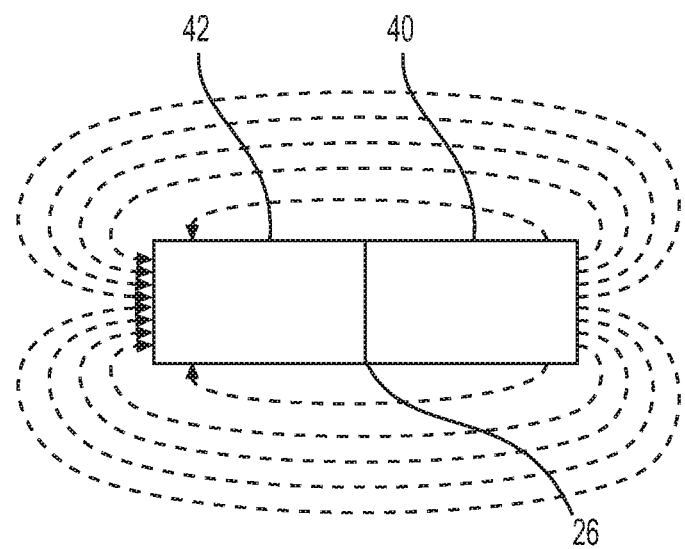
Figure 3C:
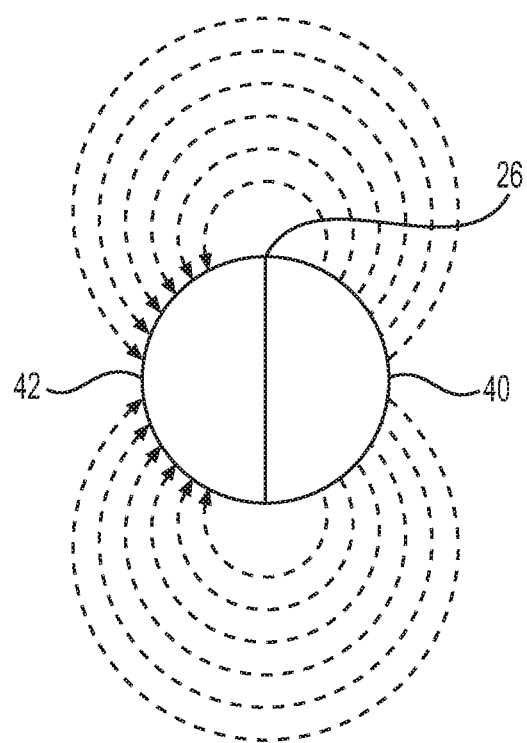

FIGS. 3A-3C show further details regarding a magnetic device 26. FIGS. 3A-3C show magnetic device 26 as a diametric magnet. However, as described above, magnetic device 26 may have any suitable shape or configuration. For example, magnetic device 26 may be an electromagnet that produces the same magnetic field as a diametric magnet. FIGS. 3A-3C show exemplary magnetic field lines of magnetic device 26. FIG. 3A shows a perspective view of magnetic device 26, FIG. 3B shows a side view of magnetic device 26, and FIG. 3B shows a top view of magnetic device 26. Magnetic field lines shown in FIGS. 3A-3C are merely schematic and do not portray the precise or specific magnetic field of magnetic device 26. Rather, they are merely exemplary and representative of a general character of possible magnetic field lines of magnetic device 26. As shown in FIGS. 3A-3C, magnetic field lines representing a magnetic field of magnetic device 26 may extend from pole 40 of magnetic device 26 to pole 42 of magnetic device 26. Pole 40 may be a north pole of magnetic device 26, and pole 42 may be a south pole of magnetic device 26. If, instead, pole 40 were a south pole and pole 42 were a north pole, then a direction of the illustrated magnetic field lines may be reversed.

Figure 4:
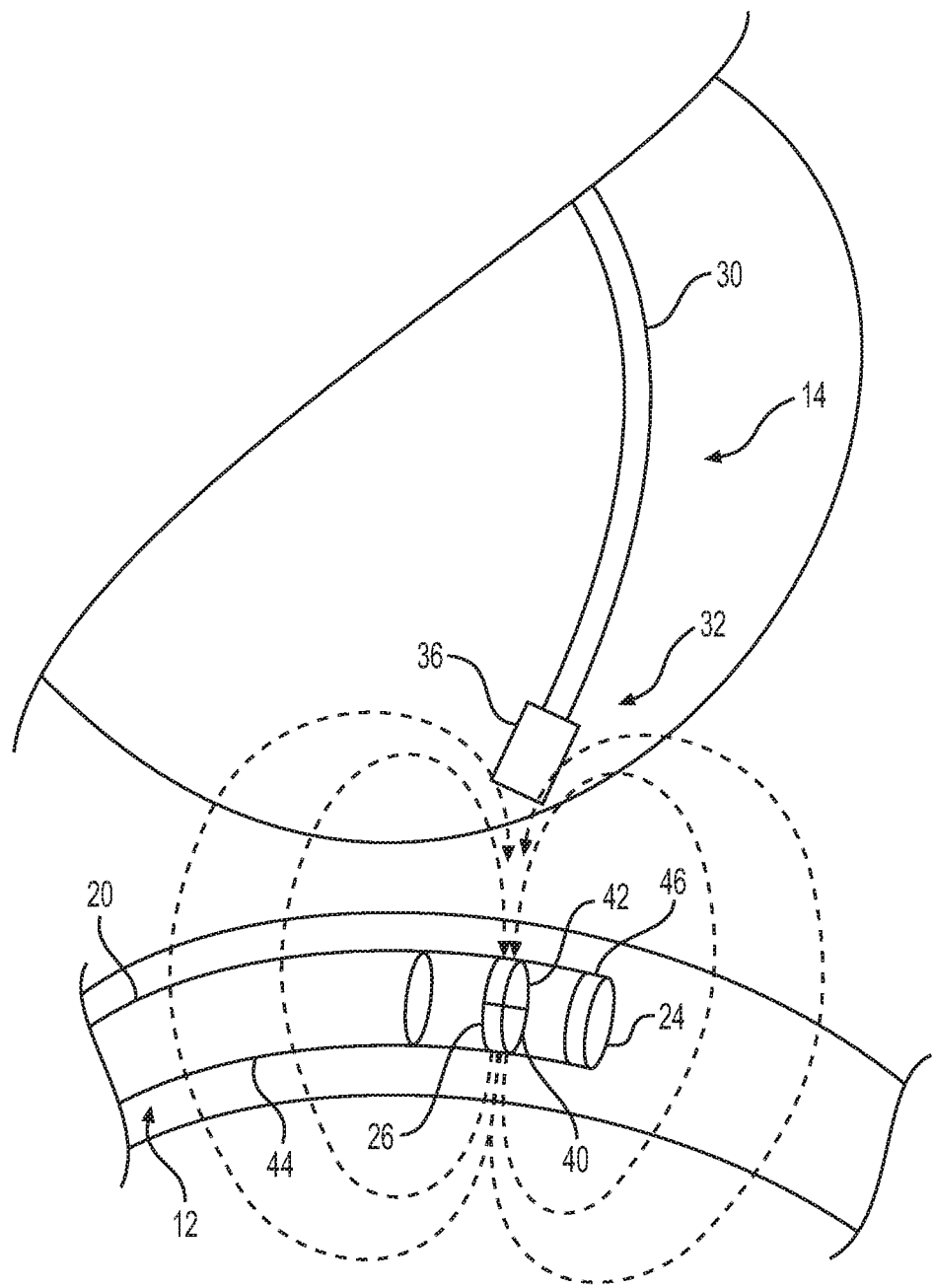
FIGS. 4-6 show exemplary systems for performing gastric bypass procedures.

FIG. 4 shows an interaction between a magnetic device 26 and a magnetic field sensor 36 when first and second devices 12 and 14 are inserted into body lumens. In an exemplary procedure, first device 12 may be inserted into an intestinal lumen of a subject. For example, a distal portion 22 of first device 12 may be inserted into a mouth of a subject, through an esophagus, through a stomach, and into a small intestine of the subject. First device 12 may include features such as those known in the art for advancing distal end 22 of first device 12 into a known location of a small intestine, such as the jejunum or the ileum. For example, distal end 22 of first device 12 may be inserted approximately 150 centimeters into a small intestine of a subject. Second device 14 may simultaneously, previously, or subsequently be inserted into a stomach lumen of the subject. A distal portion 32 of second device 14 may be inserted into a mouth of a subject and down the subject's esophagus, into the subject's stomach. Second device 14 may be advanced distally into the stomach.

Magnetic field sensor 36 may be used while second device 14 is navigated in a subject's stomach lumen. Distal portion 22 of first device 12, including magnetic device 26, may be held in place at a desired location in the small intestine lumen (e.g., 150 cm into the small intestine). An operator may receive from magnetic field sensor 36 a signal indicative of a magnetic field measured by magnetic field sensor 36. An operator of second device 14 may analyze a signal or other output from magnetic field sensor 36, looking for a signature of magnetic device 26. When a signature of magnetic device is received (e.g., by a magnetic field pointing perpendicular to a tissue wall surrounding an intestinal and/or stomach lumen, for a magnetic device 26 as depicted in FIGS. 3A-3C), then an operator may know that magnetic field sensor 36 is positioned in a portion of the stomach lumen adjacent to or proximate to a desired location in the small intestine (e.g., 150 cm into the small intestine). An operator may be able to identify a tissue wall surrounding the second lumen that is proximate to and/or adjacent to a position in the first lumen where magnetic device 26 is located. System 10 may facilitate an operator in grasping or otherwise manipulating a tissue wall surrounding the first lumen and proximate to the magnetic device 26. For example, when a magnetic device is advanced 150 cm into a small intestine past the pylorus, an operator may be able to identify a portion of a stomach wall that is proximate to or adjacent to a wall of a small intestine that is 150 cm past the pylorus. The same principles apply to other body lumens and/or other locations within body lumens.

Following recognition by magnetic field sensor 36 of an appropriate signature of a magnetic field of magnetic device 26, an operator may proceed to perform a procedure involving the identified tissue portion. A medical tool may be advanced into the second lumen from the first lumen. A portion of a tissue wall defining the first lumen may be joined to a portion of a tissue wall defining the second lumen via, for example, a perforation in a wall surrounding the second lumen. The perforation may be made proximate to the magnetic device 26. For example, a first hole may be formed in the tissue wall defining the first lumen, and a second hole may be formed in the tissue wall defining the second lumen. The tissue wall defining the first lumen may be joined to the tissue wall defining the second lumen so that the first hole and the second hole are in communication with another. A continuous lumen may be formed between the first lumen and the second lumen via the first hole and the second hole. For example, an operator may perform a gastric bypass procedure by forming a passage between a stomach and an identified portion of a patient's small intestine. A portion of a patient's stomach lumen may be joined to a portion of the intestinal lumen. Food may bypass portions of the intestinal lumen proximal to the created junction between the stomach lumen and the intestinal lumen. Food may pass through portions of the intestinal lumen distal to the created junction between the stomach lumen and the intestinal lumen. For example, food may pass through portions of the intestinal lumen greater than 150 cm from the pylorus.

Figure 5:
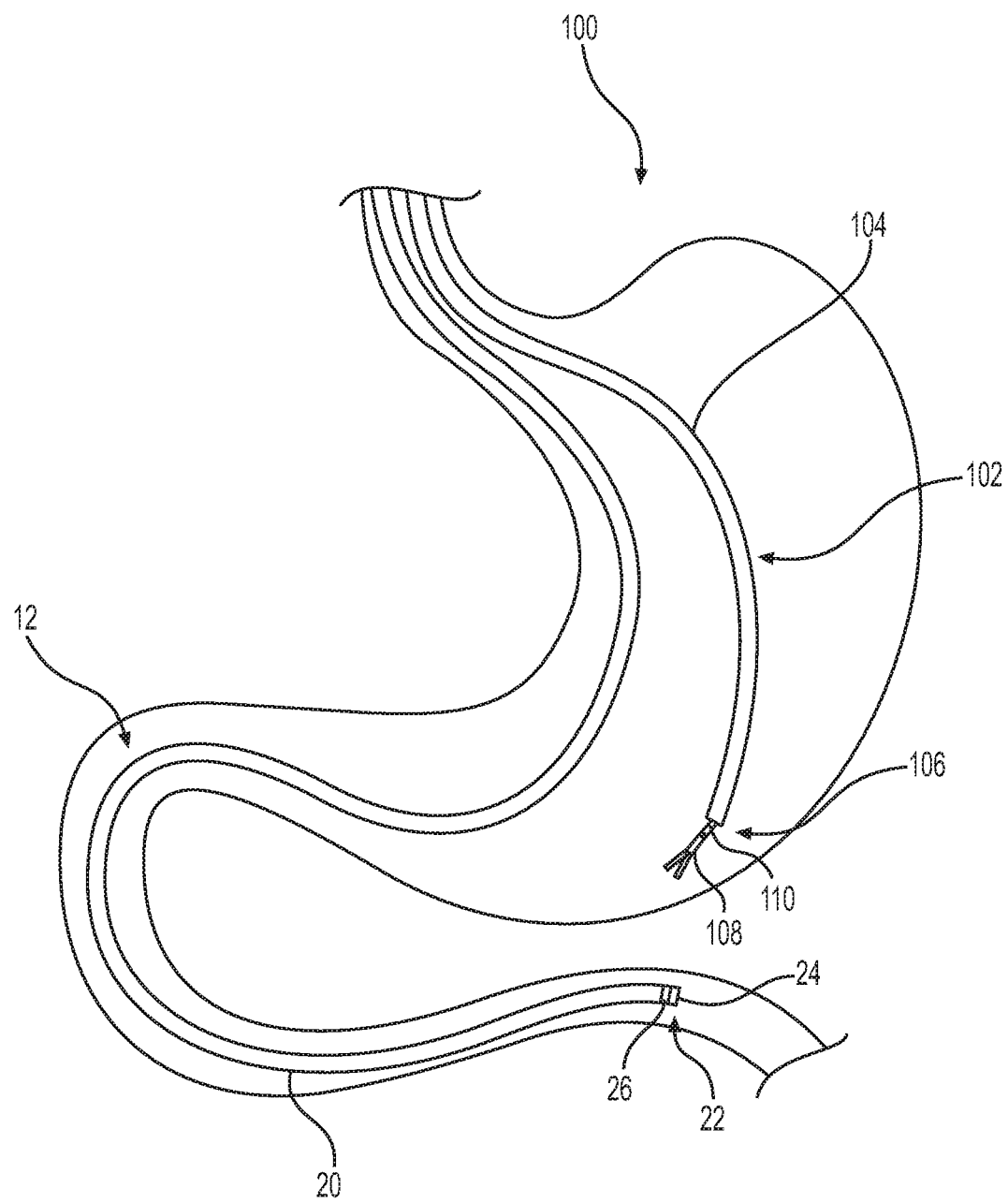

FIG. 5 shows an alternative system 100, which makes use of an alternative second device 102. Second device 102 may have any of the properties of second device 14, discussed above. Second device 102 may include an elongate member 104, which may have any of the properties of member 30, discussed above. Member 104 may have a distal portion 106, which may have any of the properties of distal portion 32. Second device 102 may also include a tool 108. Tool 108 may be any suitable form of tool that may be, for example, inserted in a working lumen of member 104 or otherwise included with member 104. Member 104 may have one or more working lumens. For example, member 104 may have a 3.8 mm working lumen and a 2.8 mm working lumen. Tool 108 may be passed through a working lumen of member 104, such as a 2.8 mm working lumen of member 104. For example, tool 108 may be an atraumatic small bowel grasper or any other type of tool.

Tool 108 may include a magnetic field sensor 110. Magnetic field sensor 110 may have any of the properties described above with regard to magnetic field sensor 36. Magnetic field sensor 110 may be disposed in any location of tool 108, such as a distal shaft of tool 108. Alternatively, magnetic field sensor 110 may be disposed on member 104. Alternatively, magnetic field sensor 110 may be a stand-alone device that may be inserted through a working lumen of member 104. Any of the methods described above with regard to FIGS. 1-4 may be used in conjunction with system 100. After or concurrent with performing such methods, tool 108 may be used in performing a procedure such as a gastric bypass procedure, either before or after tool 108 detects a magnetic field signature of magnetic device 26. For example, while first device 12 is present in an intestinal lumen (or any other body lumen) of a subject, second device 102 may be maneuvered in a stomach lumen (or any other body lumen) of a subject. Magnetic field sensor 110 may be utilized in order to detect a magnetic field emitted by magnetic device 26. Upon detecting a magnetic field emitted by magnetic device 26, an operator may be aware of a position of magnetic device 26 relative to second device 102. In order to detect the magnetic field emitted by magnetic device 26, an operator may compare data from magnetic field sensor 110 to predetermined qualities of the magnetic field (e.g., magnitude or direction) and/or may analyze data from magnetic field sensor 110 to determine, for example, that a strength or direction of the magnetic field measured is changing. Such information may be indicative of a position of magnetic device 26. For example, an operator may be aware that distal portion 106 is in a portion of a first body lumen (such as a stomach) that is proximate or adjacent to a predetermined location in a second body lumen (such as a small intestine) into which first device 12 is inserted (e.g., 150 cm distal of the pylorus). An operator may then advance and/or actuate tool 108 in order to perform a medical procedure. For example, an operator may utilize tool 108 in order to grasp a portion of a small bowel that is 150 cm from a subject's pylorus. Other suitable tools that may be used in conjunction with or as an alternative to a grasper include tools used for perforating the stomach wall and/or intestinal wall, for affixing the stomach wall to the intestinal wall, sealing the affixed walls, and/or otherwise providing an anastomosis between the stomach and intestinal walls.

Figure 6:
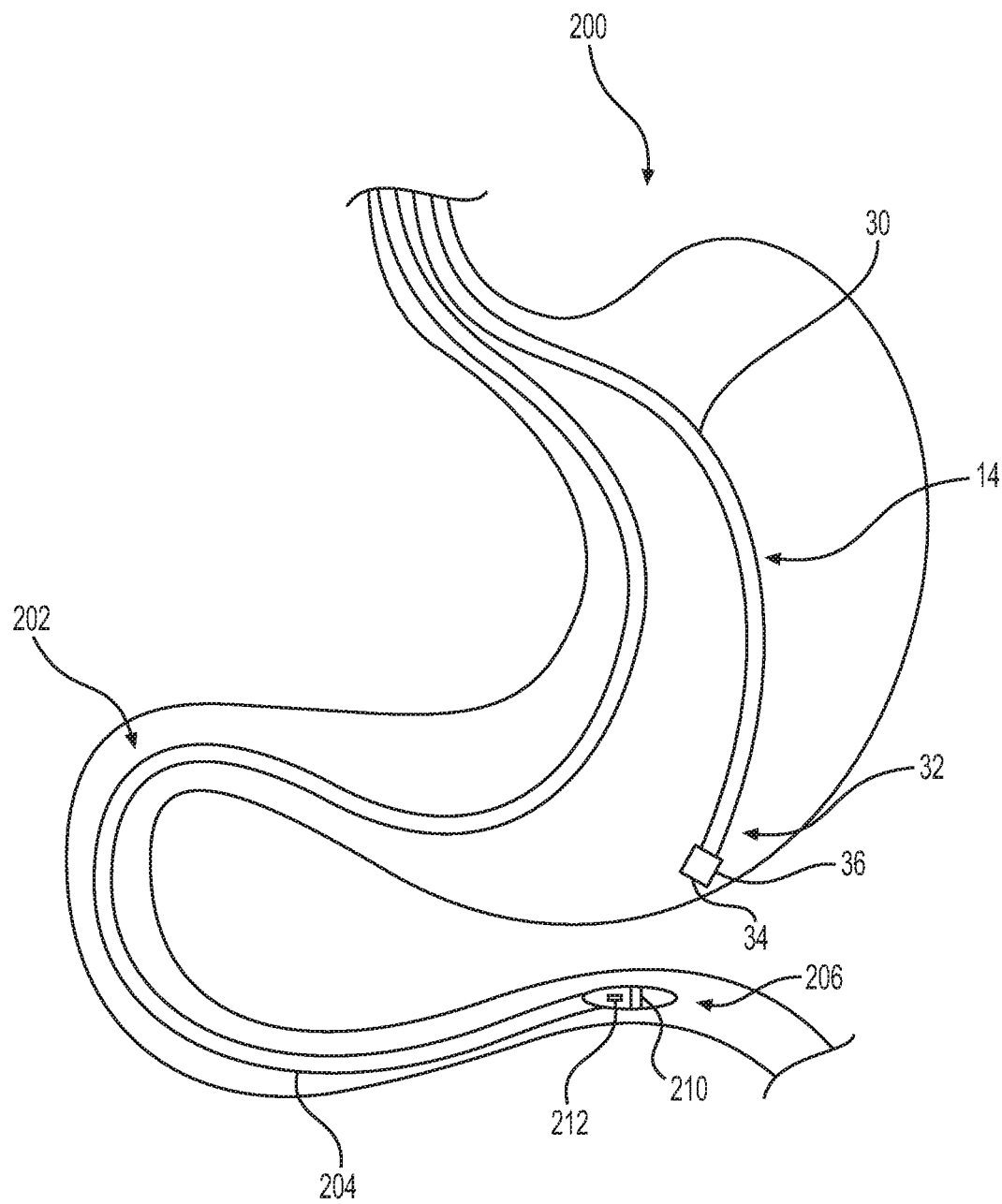

FIG. 6 shows an alternative system 200, which makes use of an alternative first device 202. Alternative first device 202 may have any of the properties of first device 12, described above. First device 202 may be used in conjunction with either of second devices 14, 102 described above or with an alternative device. First device 202 may have an elongate member or shaft 204, which may have any of the properties of member 20, described above. Member 204 may have a distal portion 206, which may have any of the properties of distal portion 22. Distal portion 206 may be have an elongate shape with one or more rounded ends. Distal portion 206 may be shaped approximately like a capsule. Distal portion 206 may make use of a thin wire connection for steering of distal portion 206. For example, two-way directional steering may be used. As opposed to using a plastic tube catheter in conjunction with distal portion 206, a small electrical wire could both tether distal portion 206 and provide length measurement and/or electricity. Such a wire could be highly flexible and small in diameter (e.g., a smaller diameter than a catheter). Distal portion 206 may include a magnetic device 210, which may have any of the properties of magnetic device 26, described above. Distal portion 206 may have any of the magnetic shielding properties of distal portion 22, described above.

Distal portion 206 may also include an illumination portion 212. Illumination portion 212 may be embedded in distal portion 206, may be within distal portion 206, may be mounted on distal portion 206, or may be affixed to distal portion 206 in any other suitable way. Illumination portion 212 may include, for example, one or more optical fibers, light emitting diodes (LEDs), or other suitable illumination device. Illumination portion 212 may be configured to emit a steady light and/or a blinking light having any pattern of blinking.

As discussed above, distal portion 36 of second device 14 may include cameras, lenses, or other optical devices. Such cameras, lenses, or other optical devices may be configured to detect light emitted from illumination portion 212. Light emitted from illumination portion 212 may be used in order to identify a portion of a body lumen of interest (e.g., a portion of the small bowel approximately 150 cm from the pylorus), in isolation or in conjunction with magnetic device 210. For example, an operator my be able to visualize light emitted from illumination portion 212 through a wall of a stomach lumen. Illumination portion 212 may be configured so as to focus emission of light toward a wall of a lumen facing second device 14. An operator may also make use of a signal from magnetic field sensor 36.

Figure 7:
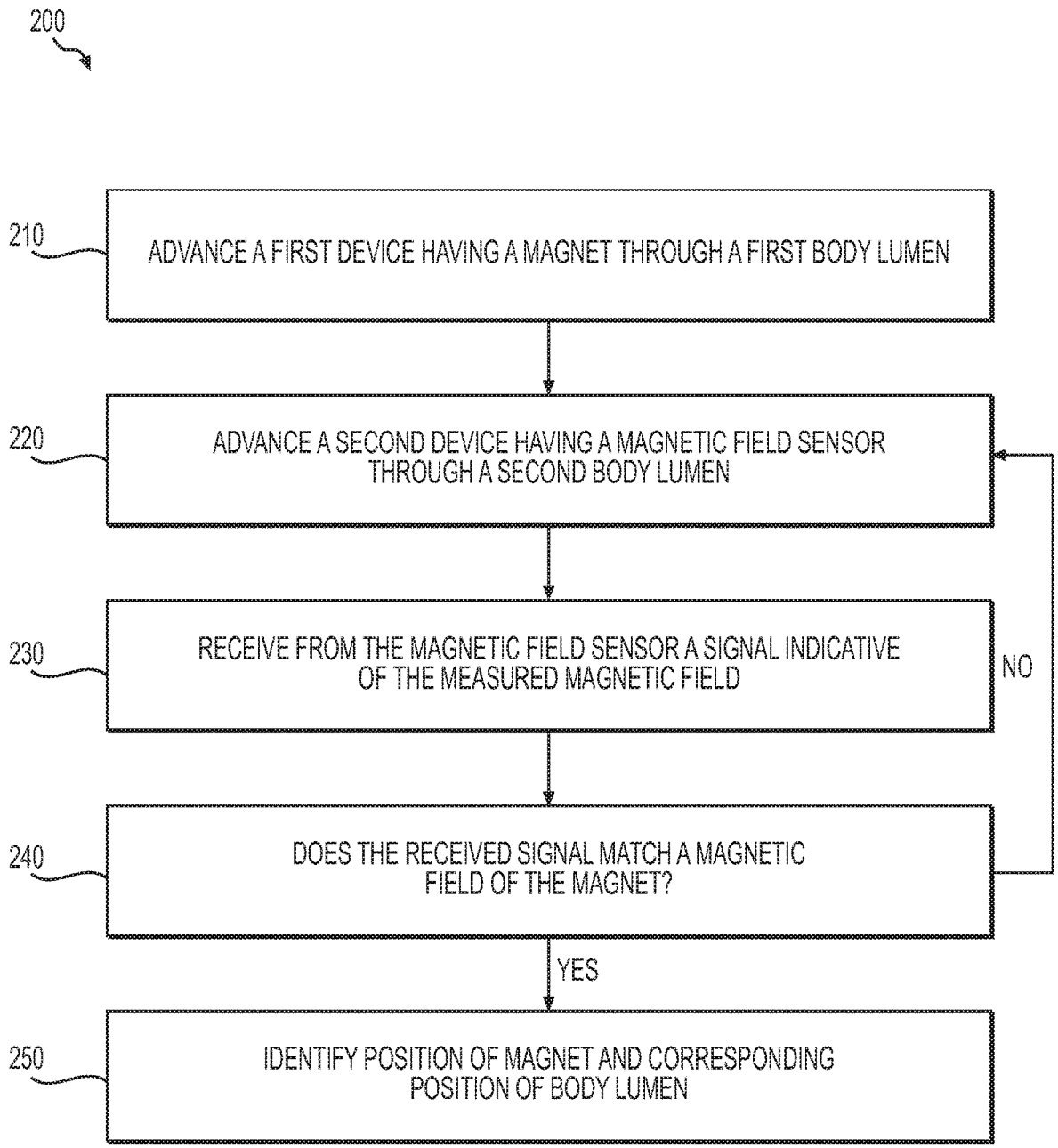
FIG. 7 shows a flow chart of an exemplary medical procedure.

FIG. 7 shows an exemplary method for performing a medical procedure, which may be used with any of the above method steps, devices, or systems. As shown in FIG. 7, a method 200 for performing a medical procedure such as a gastric bypass procedure may involve, in step 210, advancing a first device (e.g., first device 12 or first device 202) through a first body lumen, such as a small bowel lumen. First device 12 or 202 may be advanced to a predetermined portion of the body lumen, corresponding to a location where an operator desires to manipulate the tissue surrounding the body lumen. As described above, first device 12 or 202 may include a magnetic device such as magnetic device 26 or 210, which may be, e.g., a permanent magnet or an electromagnet. In step 220, an operator may advance a second device, such as second device 14 or second device 102 through a second body lumen (e.g., a stomach). As described above, second device 14 or 102 may include a magnetic field sensor, such as magnetic field sensor 36 or 110, which may be, e.g., a permanent magnet or an electromagnet. In step 230, an operator may receive a signal from a magnetic field sensor 36 or 110. The received signal may be indicative of a measured magnetic field and may include information relating to a direction of a detected magnetic field, a magnitude of a detected magnetic field, or both. In step 240, it may be determined whether the signal received in step 230 matches a magnetic field of magnetic device 26 or 210 (such as those described above). For example, it may be determined whether a direction of the signal received in step 230 matches a predetermined direction or a predetermined signature. Additionally or alternatively, whether the received signal matches a magnetic field of magnetic device 26 and/or 210 may be determined by analyzing changes in a reading from a magnetic field sensor 36 or 110. For example, a magnetic field of magnetic device 26 or 210 may be matched by locating the strongest measured field or by locating another characteristic feature of magnetic device 26 or 210.

If the received signal does match the magnetic field, then, in step 250, the position of the magnet may be identified in the first body lumen. Based on that information, a predetermined area of interest in the first body lumen (or the second body lumen) may be identified. For example, an operator may identify an area of interest in a tissue wall surrounding the second body lumen or may identify a portion of the first body lumen (and/or surrounding tissue) that should be manipulated. If, in step 240, the received signal does not match the magnetic field, then step 220 may be repeated in order to move the second device 14 or 102 to a new portion of the second body lumen and again analyze the magnetic field measured there.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method for performing a medical procedure, comprising:
    advancing a first device through a first body lumen to a portion of the first body lumen, wherein a distal portion of the first device includes a magnet;
    advancing a second device through a second body lumen, wherein the second device includes a magnetic field sensor;
    receiving a signal from the magnetic field sensor, wherein a controller receives the signal, and wherein the signal is indicative of a magnetic field measured by the magnetic field sensor; and
    based on the received signal, joining the portion of the first body lumen to the second body lumen.

2. The method of claim 1, further comprising identifying a location of a tissue wall surrounding the first body lumen, wherein the location is proximate to the magnet.

3. The method of claim 1, wherein the first body lumen is a small bowel lumen, and wherein the second body lumen is a gastric lumen.

4. The method of claim 1, further comprising grasping a wall surrounding the first body lumen proximate to the portion of the first body lumen.

5. The method of claim 1, wherein the magnetic field has a direction perpendicular to a tissue wall defining the first body lumen.

6. A method for performing a medical procedure, comprising:
- advancing a first device through a first body lumen, wherein a distal portion of the first device includes a magnet;
- advancing a second device through a second body lumen, wherein the second device includes a magnetic field sensor;
- receiving a signal from the magnetic field sensor, wherein a controller receives the signal, and wherein the signal is indicative of a magnetic field measured by the magnetic field sensor; and
- based on the received signal, advancing a medical tool from the second body lumen into the first body lumen.

7. The method of claim 6, further comprising identifying a location of a tissue wall surrounding the first body lumen, wherein the location is proximate to the magnet.

8. The method of claim 6, wherein the first body lumen is a small bowel lumen, and wherein the second body lumen is a gastric lumen.

9. The method of claim 6, wherein the magnetic field has a direction perpendicular to a tissue wall defining the first body lumen.

10. A method for performing a medical procedure, comprising:
- advancing a first device through a first body lumen to a portion of the first body lumen, wherein a distal portion of the first device includes a magnet;
- advancing a second device through a second body lumen, wherein the second device includes a magnetic field sensor;
- receiving a signal from the magnetic field sensor, wherein a controller receives the signal, and wherein the signal is indicative of a magnetic field measured by the magnetic field sensor; and
- based on the received signal, providing an anastomosis between the portion of the first body lumen and the second body lumen.

11. The method of claim 10, further comprising identifying a location of a tissue wall surrounding the first body lumen, wherein the location is proximate to the magnet.

12. The method of claim 10, wherein the first body lumen is a small bowel lumen, and wherein the second body lumen is a gastric lumen.

13. The method of claim 10, further comprising grasping a wall surrounding the first body lumen proximate to the portion of the first body lumen.

14. The method of claim 10, wherein the signal includes information regarding at least one of a direction or a magnitude of the magnetic field.

15. The method of claim 10, wherein the magnet is a diametrical magnet.

16. The method of claim 10, wherein the first device includes at least one magnetically shielded portion.

17. The method of claim 10, wherein the second device further includes an atraumatic grasper.

18. The method of claim 10, wherein the distal portion of the first device further includes a light emitting source, and the method further comprises detecting a light emitted by the light emitting source.

19. The method of claim 10, further comprising:
- forming a first hole in a first tissue wall defining the first body lumen;
- forming a second hole in a second tissue wall defining the second body lumen; and
- creating a junction between the first hole in the first tissue wall and the second hole in the second tissue wall such that the first hole is in communication with the second hole.

20. The method of claim 10, wherein the magnetic field has a direction perpendicular to a tissue wall defining the first body lumen.

* * * * *